United States Patent [19]

Tury

[11] Patent Number: 5,567,341
[45] Date of Patent: Oct. 22, 1996

[54] AMMONIUM ORGANO-PHOSPHORUS ACID SALTS

[75] Inventor: Bernard Tury, Manchester, United Kingdom

[73] Assignee: Imperial Chemical Industries PLC, United Kingdom

[21] Appl. No.: 381,852

[22] PCT Filed: Jul. 13, 1993

[86] PCT No.: PCT/GB93/01464

§ 371 Date: Apr. 18, 1995

§ 102(e) Date: Apr. 18, 1995

[87] PCT Pub. No.: WO94/03462

PCT Pub. Date: Feb. 17, 1994

[30] Foreign Application Priority Data

Aug. 7, 1992 [GB] United Kingdom ............ 9216780

[51] Int. Cl.$^6$ ............ C10M 105/74; C07F 9/165
[52] U.S. Cl. ............ 508/436; 558/208; 558/214; 508/476
[58] Field of Search ............ 252/32.5, 32.7 R, 252/32.7 E; 558/208, 214

[56] References Cited

U.S. PATENT DOCUMENTS

| | | | |
|---|---|---|---|
| 3,718,588 | 2/1973 | Bellos et al. | 252/32.5 |
| 4,289,634 | 9/1981 | Lewis et al. | 252/32.5 |
| 4,977,294 | 12/1990 | Uphues et al. | 558/208 |
| 5,073,277 | 12/1991 | Wirth et al. | 252/32.7 R |

FOREIGN PATENT DOCUMENTS

| | | |
|---|---|---|
| 0157731 | 10/1985 | European Pat. Off. . |
| 0277711 | 8/1988 | European Pat. Off. . |
| 1373660 | 11/1974 | United Kingdom . |

*Primary Examiner*—Jerry D. Johnson

[57] ABSTRACT

Novel ammonium salts of organo-oxyphosphorus acids, organo-thiophosphorus acids and their esters and to the use thereof as additives for lubricants, especially for providing protection against extreme pressure and corrosion, to compositions containing these novel salts, a method for lubricating metal surfaces in frictional contact, and a metal surface treated with the salt or lubricant composition.

10 Claims, No Drawings

AMMONIUM ORGANO-PHOSPHORUS ACID SALTS

The present invention relates to novel ammonium salts of organo-oxyphosphorus acids, organo-thiophosphorus acids and their esters and to the use thereof as additives for lubricants, especially for providing protection against extreme pressure and corrosion, to compositions containing these novel salts, a method for lubricating metal surfaces in frictional contact, and a metal surface treated with the salt or lubricant composition.

In EP 277,711 there is disclosed a method for protecting metal surfaces against corrosion by treating the metal surface with the reaction product of a polyester and an amine or salt thereof with an organic acid, chloride or sulphate.

It is also known to improve the wear resistance of metal surfaces by incorporating ammonium salts of organophosphorus acid derivatives in lubricating oil compositions. Thus, it has been proposed in U.S. Pat. No. 4,962,227 to use ammonium salts of methyl phosphonic acid as lubricant additives and in U.S. Pat. No. 4,514,311 to use specific ammonium salts of phosphate esters for a similar purpose.

None of these compounds are wholly satisfactory under all operating conditions, particularly under extreme pressure. It has now been found that ammonium salts of organo-oxyphosphorus acids, organo-thiophosphorus acids and their esters with the polyesteramine disclosed in EP 277,711 are especially effective as lubricant additives and provide a number of desirable properties, especially when incorporated in lubricating oils and greases.

According to the present invention there is provided an ammonium salt of an organo-oxyphosphorus acid, an organo-thiophosphorus acid or esters thereof (hereinafter referred to as the "Polyester ammonium salt") with a polyesteramine of Formula I

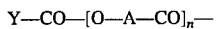

Y—CO—[O—A—CO]$_n$—Z—R    I wherein

A is a divalent hydrocarbon radical;

Y is a hydrogen atom or an optionally substituted hydrocarbon group;

n is an integer from 1 to 100;

Z is a divalent bridging group; and

R is an amino group.

The precise structure of the chain terminating group Y not critical provided it is inert to the other components of the composition under the normal processing conditions to which it is subjected. It is preferably free from ionic and strongly polar groups and preferably has a molecular weight of less than 300 and contains only C and H or C, H and O atoms.

The group Y is preferably alkyl or alkenyl containing up to 35 carbon atoms, especially from 7 to 25, and more especially from 7 to 20 carbon atoms such as heptyl, octyl, undecyl, lauryl, heptadecyl, heptadecyl, heptadecadienyl, stearyl, oleyl, linoleyl or such a group substituted by a hydroxy, halo or alkoxy group, especially $C_{1-4}$ alkoxy. Particularly preferred terminal groups Y—CO— are 12-hydroxystearyl and 12-hydroxyoleyl. Other values for Y include, $C_{4-8}$-cycloalkyl, such as cyclohexyl; polycycloalkyls, for example, polycyclic terpenyl groups which are derivable from naturally occurring acids such as abietic acid; aryl, such as phenyl; aralkyl, such as benzyl and polyaryl, such as naphthyl, biphenyl, stilbenyl and phenylmethylphenyl. Such groups are preferably unsubstituted or substituted by a group selected from hydroxy, halogen and $C_{1-4}$ alkoxy.

The divalent hydrocarbon group represented by A may be an aromatic group but is preferably an alkylene or alkenylene group, especially one containing from 4 to 25 carbon atoms with at least 4 carbon atoms between the oxygen atom and carbonyl group. Preferably n has a value of at least two. When n is greater than one, the groups represented by A in the polyester chain [O—A—CO]$_n$ may be the same or different.

It is generally preferred that n is from 1 to 10, and especially from 1 to 6, when the group A is an aliphatic chain containing nine or more carbon atoms and n is from 1 to 60 when the group A is an aliphatic chain containing up to eight carbon atoms. The groups represented by A may carry other substituents which do not confer water-solubility on the molecule, such as halogen and alkoxy. Preferred examples of the group (—O—A—CO—) are 12-oxystearyl, 12-oxyoleyl and 6-oxycaproyl.

The polyester residue of the formula:

Y—CO—[O—A—CO]$_n$—    II is conveniently derived from a mixture of (i) a saturated or unsaturated aliphatic hydroxycarboxylic acid containing from 4 to 25 carbon atoms having at least 4 carbon atoms between the hydroxy and carboxyl groups or a cyclic precursor thereof, such as a lactone and (ii) an aliphatic carboxylic acid of the formula Y—COOH, where Y is as hereinbefore defined.

Examples of suitable hydroxycarboxylic acids and precursors are 12-hydroxystearic acid, 12-hydroxy-9-oleic acid (or ricinoleic acid), 6-hydroxycaproic acid and E-caprolactone.

Examples of suitable acids from which the end group —Y—CO— is derivable, by reaction with a terminal hydroxy group on the polyester chain, are lauric acid, palmitic acid, stearic acid and 9-oleic acid and mixtures containing these acids which are derivable from natural products.

The divalent bridging group, Z, is preferably of the formula:

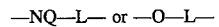

—NQ—L— or —O—L— wherein

Q is a hydrogen atom or an alkyl group and L is an alkylene or hydroxyalkylene group, or N, Q and L, together with the nitrogen atom in the group R to which they are attached form a cycloaliphatic bridging group.

The group Q preferably contains up to 25 carbon atoms. The alkylene group which is, or which is present in, the group L preferably contains from 2 to 6 carbon atoms.

Examples of the group represented by Q are methyl, ethyl, n-propyl, n-butyl and octadecyl and of the group represented by L are —(CH$_2$)$_2$—, —(CH$_2$)$_3$—, —(CH$_2$)$_4$—, —(CH$_2$)$_6$—, and —CH$_2$—CHOH—CH$_2$— and an example of the cycloaliphatic bridging group is piperazin-1,4-ylene.

The amino group R may be a primary, secondary or tertiary amino group and is preferably of the formula:

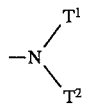

wherein $T^1$ and $T^2$ are independently hydrogen, $C_{1-22}$ alkyl, substituted $C_{1-22}$ alkyl, alkaryl or cycloalkyl; or $T^1$ and $T^2$ may together with the nitrogen atom to which they are attached form a 5- or 6-membered ring.

When $T^1$ or $T^2$ is alkyl, it is preferably $C_{1-6}$ alkyl, such as methyl. When $T^1$ and $T^2$ form a ring it is preferably a piperidino, morpholino or especially an N-alkyl piperazino ring. When $T^1$ or $T^2$ is alkaryl, it is preferably benzyl. When the bridging group Z is a cycloaliphatic, one of $T^1$ or $T^2$ is incorporated into the bridging group. Thus, the group —Z—R may be of the formula

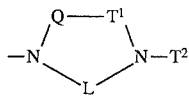

It is preferred that both $T^1$ and $T^2$ are other than hydrogen, so that R is tertiary amino.

The Polyesteramine can be prepared by processes described in UK Patent Nos 1342746, 1373660 and 2001083 and EP 127325 (with omission of the epoxidation).

The Polyesterammonium salt may be derived from the Polyesteramine alone or the latter may be used in admixture with a polyester of general formula III (hereinafter referred to as the "Polyester"),

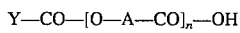

where A, Y and n are as hereinbefore defined.

Such a mixture is conveniently obtained by reaction of the Polyester with less than the quantity of an amine necessary to completely convert the Polyester into the desired Polyesteramine. It is generally more convenient to prepare such a mixture than the pure Polyesteramine and it has been shown that Polyesterammonium salts prepared from such a mixture are effective lubrication additives.

The acid from which the Polyesterammonium salt may be derived is conveniently an organo-oxyphosphorus acid or organo-thiophosphorus acid (hereinafter referred to as the Acid) or a partial ester thereof of Formula IV

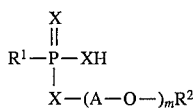

wherein $R^1$ is hydrogen, optionally substituted $C_{1-30}$ hydrocarbyl, a group —X—(A—O—)$_m$R$^2$ or a group —X—P(X)—(XR$^2$)$_2$;

$R^2$ is hydrogen or optionally substituted $C_{1-30}$ hydrocarbyl;

A—O— is $C_{2-6}$ alkyleneoxy; m is 0 to 50; and

X is oxygen or sulphur;

provided that when m is zero, $R^1$ and $R^2$ are not both hydrogen.

The group $R^1$ is preferably $C_{5-20}$ hydrocarbyl, and more especially $C_{5-14}$ hydrocarbyl. The group $R^1$ may be selected from alkyl which may be linear or branched, aralkyl, alkaryl, aryl, cycloalkyl, alkenyl and alkynyl groups. Examples of suitable alkyl group are methyl, ethyl, n-propyl, n-butyl, isobutyl, sec-butyl, amyl, hexyl, octyl, nonyl, 2-ethylhexyl, octyl, decyl, 2-hexyldecyl and octadecyl. Examples of aralkyl are benzyl and 2-phenylethyl. Examples of cycloalkyl are cyclohexyl, cycloheptyl, cyclooctyl, 2-methylcycloheptyl, 3-butyl-cyclohexyl and 3-methylcyclohexyl. Examples of aryl are phenyl and naphthyl. Examples of alkenyl are vinyl, amyl but-1-enyl, dodecenyl, octadecenyl and octadecadienyl. Examples of alkynyl are ethynyl, propynyl and butynyl. Any substituent present in $R^1$ should not, of course, adversely effect the desirable properties of the Polyesterammonium salt or a lubricant additive. Preferred substituents are selected from halogen, especially chlorine and bromine; alkyl, especially $C_{1-4}$ alkyl; nitrile; trifluoromethyl; $R^1CO$; $R^1O$; $R^1OCO$ and $R^1COO$ groups. It is preferred that $R^1$ is unsubstituted and is especially alkyl or cycloalkyl.

When $R^2$ is optionally substituted $C_{1-30}$ hydrocarbyl, it is as defined for $R^1$.

A preferred class of the Acid comprises a phosphonic acid of Formula V and mono esters thereof

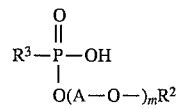

wherein $R^3$ is optionally substituted $C_{1-30}$ hydrocarbyl; and $R^2$, A—O— and m are as hereinbefore defined.

Examples of phosphonic acids of formula V and monoesters thereof are methyl, octyl, in particular n-octyl, 2-ethylhexyl, decyl, dodecyl, tetradecyl, phenyl and benzyl phosphonic acids and the monoethyl ester of octylphosphonic acid and the mono(2-ethylhexyl) ester of 2-ethylhexylphosphonic acid.

A further preferred class of the Acid comprises phosphorous acid esters of Formula VI

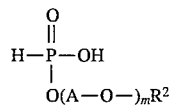

wherein $R^2$, A—O— and m are as hereinbefore defined; provided that when m is zero $R^2$ is not hydrogen.

An example of a phosphorous acid ester is the mono octyl ester.

A further preferred class of the Acid comprises pyrophosphates of formula VII

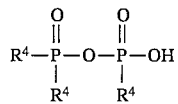

wherein each $R^4$ is independently a group —O—(A—O—)$_m$R$^2$; and $R^2$, A—O— and m are as hereinbefore defined;

provided that when m is zero, at least one $R^2$ is not hydrogen.

Examples of suitable pyrophosphates are mono- and di-octyl and dihexyl pyrophosphates.

An especially preferred class of the Acid comprises mono- and di-esters of phosphoric acid of Formula VIII, and mixtures thereof

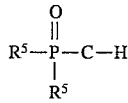

wherein each $R^5$ is independently a group —O—(A—O—)$_m$R$^2$; and $R^2$, A—O— and m are as hereinbefore defined;

provided that when m is zero, both $R^2$ are not hydrogen.

Examples of phosphoric acid esters include the bis(cyclohexyl), dihexyl, bis(2-ethylhexyl), dibenzyl, didodecyl, diisooctyl, dioctadecyl and diphenyl esters.

Examples of phosphoric acid esters also include the monododecyl, mono 2-ethylhexyl, mono isooctyl, mono decyl, mono hexadecyl, including the mono 2-hexyldecyl, and mono octadecyl including the mono iso-octadecyl, esters.

Examples of phosphoric acid esters further include the bis and mono-esters of alkyleneoxy derivatives of $R^2OH$ such as the phosphate esters of ethoxylated phenols, ethoxylated 2-ethylhexanol, ethoxylated 4-nonylphenol and ethoxylated $C_{6-20}$ alcohols and ethoxylated $C_{6-20}$ amines.

Phosphoric acid esters of alkoxylated alcohols, amines and phenols of this type are commercially available as COPTAL, LENETOL and SUNAPTOL surfactants. (COPTAL, LENETOL and SUNAPTOL are trade marks, the property of ICI).

An especially preferred class of the Acid comprises phosphorodithioic acid of Formula IX, and partial esters thereof

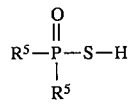     IX wherein each $R^5$ is independently the group —O—(A—O—)$_m R^2$; and $R^2$, A—O— and m are as hereinbefore defined;

provided that when m is zero, both $R^2$ are not hydrogen.

Examples of phosphorodithioic acid esters are the O,O-diethyl; O,O-bis(2-ethylhexyl); O-butyl-O-hexyl; mixed O,O-di-$C_{1-4}$ alkyl; O,O-di-nonylphenol; O,O-di-isodecyl; O,O-dioctyl and O,O-diisopentyl esters.

A still further preferred class of the Acid comprises phosphorothioic acid of Formula X, and partial esters thereof.

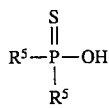     X wherein each $R^5$ is independently the group —O—(A—O—)$_m R^2$; and $R^2$, A—O— and m are as hereinbefore defined;

provided that when m is zero, both $R^2$ are not hydrogen.

Examples of suitable phosphorothioic acid esters are the O,O-dimethyl diester, O,O-dioctyl diester and O,O-bis(2-ethylhexyl) diester.

The hydrocarbyl substituent $R^2$ in Formulae IV–X is selected so as to render the Polyesterammonium salt compatible with, and more especially soluble in, the lubricant. The compatibility of the Polyesterammonium salt with the lubricant or solubility in the lubricant may be varied by altering the length and nature of the group —(A—O—)$_m$. Thus, the group —(A—O—)$_m$ may be a monomer, a homo- or block oligomer or a co-polymer derived from ethylene oxide, propylene oxide and/or butylene oxide.

The Acid of general formula V may be prepared by the reaction of an olefin with a phosphite. Thus, for example, tetradecene may be reacted with a molar excess of dimethylphosphite in the presence of a radical generator such as ditertiarybutyl phenoxide at 130°–150° C. to give tetradecylphosphonic acid (Formula V, $R^2$ is a hydrogen, $R^4$ is $C_{14}H_{29}$ and m is zero).

Phosphate mono- and di- esters of general formula VI to X may be made by reacting a hydroxy compound $R^2(A—O—)_m$—OH with phosphorus pentoxide at an elevated temperature or pyrophosphoric acid at room temperature in appropriate proportions, optionally in the presence of an inert organic solvent.

The diesters are typically prepared by reacting excess hydroxy compound with phosphorus pentoxide. Thus, dihexylphosphate (Formula VIII, $R^2$ is $C_6H_{13}$, m is zero) may be prepared by reacting 3 moles of hexanol with 1 mole of phosphorus pentoxide. The phosphorodithioic acid esters are prepared in analogous manner by replacing the phosphorus pentoxide with phosphorus pentasulphide.

The Polyesterammonium salt may be prepared by mixing together the Polyesteramine and the Acid or ester thereof in such relative proportions necessary to partially or fully neutralise the Acid or ester. This is conveniently carried out by determining the 'base' value of the Polyesteramine and the 'acid' value of the Acid or ester and mixing the two components together in all appropriate proportions necessary to replace some or available hydrogen atoms in the Acid or ester.

The 'base' value of the Polyesteramine derivative is conveniently determined by titration with a strong inorganic acid such as perchloric acid in an organic solvent such as glacial acetic acid, or hydrochloric acid.

The 'acid' value of the Acid or ester is conveniently determined by titration with a strong inorganic base such as potassium hydroxide in aqueous ethanol solution or tetraethylammonium hydroxide in propan-2-ol, in the presence of an appropriate indicator, for example, bromophenol blue, phenolphthalein or 1-naphthophthalein. The acid value determined by bromophenol blue is used to provide a part neutralised salt and the acid value determined by phenolphthalein or 1-naphthophthalein is used to provide a fully neutralised salt.

The 'base' value of the Polyesteramine and 'acid' value of the Acid or esters thereof is conventionally expressed in mg of KOH/g.

The salts obtained are hereinafter referred to as fully or partially neutralised depending on the extent of neutralisation of the Acid or ester by the Polyesteramine.

Formation of the Polyesterammonium salt can be effected at any temperature from 20° C. to 200° C., optionally in the presence of a material such as tetrabutyl titanate.

However, the salt is preferably formed at a temperature from 50° to 150° C. and especially from 70° to 120° C. At elevated temperatures the Polyesteramine salt is generally formed within about 60 minutes.

Purification of the Polyesterammonium salt, such as separation from unreacted starting materials, is not normally required provided the Polyesteramine and Acid or ester are mixed in appropriate proportions.

The Polyesterammonium salt may be formed from mixtures of different Polyesteramines and/or also mixtures of different Acids or esters thereof.

A particularly useful Polyesterammonium salt is the fully neutralised salt formed by heating (a) the reaction product of 2 moles of poly(12-hydroxystearic acid) (acid value of 35 mg KOH/gm) and 1 mole of dimethylaminopropylamine with (b) an equivalent amount of di-n-hexylphosphate.

The preparation of (a) is described in Comparative Example C of EP 127,325, omitting the quaternisation stage with dimethylsulphate.

The Polyesterammonium salt is useful as an additive for lubricants in which it can provide protection against wear of surfaces in contact, protection against deposition of sludge, resistance to extreme pressure experienced in bearings and resistance to oxidation and corrosion.

Lubricants in which the Polyesterammonium salt may be used include oils and greases for protecting metal surfaces in frictional contact. The Polyesterammonium salt may be used at a concentration from 0.01 to 10% by weight, based on the total weight of the lubricant. As a further feature of the invention there is provided a lubricant composition comprising a lubricant containing from 0.01 to 10%, preferably from 0.05 to 5% and especially from 0.1 to 2% by weight of the Polyesterammonium salt.

The lubricant may be an oil or grease.

The term oil includes oils such as those described in standard texts on lubrication such as "Schmiermittel-Taschenbuch" by Schewe-Kobek, (Huethig Verlag, Heidelberg 1974), and in "Schmierstoffe and Verwandte Produkte" by D. Klamann, (Verlag Chemie, Weinhelm 1982).

The oil is preferably a mineral oil or a synthetic oil or a mixture thereof.

Examples of such oils include poly(alkyleneglycols); poly(alpha-olefins); esters, especially phthalates, such as iso-tridecyl phthalate, perfluoroalkylethers and silicones.

The oil may contain a hydrofluorocarbon, hydrochlorofluorocarbon or chlorofluorocarbon or mixtures thereof such as are used in mechanical vapour recompression, heat transfer devices.

Preferred lubricants are those used industrially, especially gear and hydraulic oils.

The oil may contain other additives which are generally incorporated in fluid lubricants, such as metal passivators, viscosity-index improvers, pour-point depressants, dispersing agents, detergents, and different additives providing protection against wear, extreme pressure, corrosion, rusting and oxidation.

Examples of additives are such disclosed in EP 398,843 and U.S. Pat. No. 4,962,227. More specifically, the oil may contain the anti-corrosion composition described in EP 455,451.

The grease is preferably a mineral or synthetic oil as hereinbefore described which has been thickened by the addition of a gelling agent.

The gelling agent may be a soap, such as a lithium soap, a lithium complex soap, a non-soap gelling agent such as a clay, a carbon black, a silica or a polyurea which is preferably incorporated into the oil in finely divided form.

Any clay is preferably surface-coated with an organic material such as a quaternary ammonium compound.

Where the grease is based on a silicone oil, the non-soap gelling agent is preferably silica, especially fused silica having an average particle diameter below one micron.

Metals which benefit from the protection of the Polyesterammonium salt and lubricant compositions containing the Polyesterammonium salt include iron and steel and especially copper and brass where the Polyesterammonium salt has been found less aggressive than many commercially available lubricant additives with this latter group of metals.

The Polyesterammonium salt has been found particularly effective when the metal surfaces in frictional contact are part of a bearing.

Thus, according to a further feature of the invention there is provided a metal surface, particularly a bearing, treated with the Polyesterammonium salt or a lubricant composition containing the Polyesterammonium salt.

As the Polyesterammonium salt also exhibits anti-corrosion and anti-oxidant properties it may be applied to metal surfaces in an appropriate carrier as described for example in EP 455415.

The invention is further illustrated in the following examples in which all parts and percentages are by weight unless otherwise stated.

EXAMPLE 1

Antiwear Agent 1

A) Preparation of Polyesteramine (PED)

The Polyesteramine was obtained by the reaction of two mole of poly(12-hydroxyoctadecanoic acid) of molecular weight about 1600 (as determined by titration) with one mole of 1-amino-3-N,N-dimethylaminopropane as described in Comparative Example C of EP 127,325.

This amine when titrated with 0.1M perchloric acid in glacial acetic acid, had an 'base' value of 15.69 mg KOH per gram.

B) Preparation of Hexyl Phosphate (HP)

A mixture of mono and di-n-hexyl phosphate was prepared by reacting three mole of n-hexanol with one mole of phosphorous pentoxide.

This material when titrated with 0.1M alcoholic potassium hydroxide solution using 1-naphthophthalein as indicator had an 'acid' value of 377.9 mg KOH per gram.

C) Preparation of Antiwear Agent 1

A mixture of 0.41g of HP and 9.59g PED was heated at 100° C. for approximately one hour to ensure reaction. This gave a fully neutralised (FN) organophosphorus salt of PED.

EXAMPLE 2

Lubricant 1

A lubricant composition was prepared by adding 1 part of Antiwear Agent 1 to 99 parts of a solvent neutral base oil (viscosity 24 $mm^2s^{-1}$ at 40° C.; sulphur content 1.6%).

EXAMPLE 3

A sample of Lubricant 1 was subjected to a four ball antiwear test based on IP239 (temperature 75° C.; time 1 hour; Load 40 Kg) using the same solvent neutral base oil as control. At the end of the test the average wear scar diameters (WSD) were measured and these are recorded in Table 1.

TABLE 1

| Example | Additive | WSD (mm) |
| --- | --- | --- |
| 3 | Antiwear Agent 1 | 0.44 |
| Control | Nil | 1.16 |

EXAMPLE 4

Antiwear Agent 2

A) Preparation of Mono 2-Hexyldecyl Phosphate (PMH)

This phosphate was prepared by reacting 2-hexyldecanol (242 g) (Eficay Chemicals) with pyrophosphoric acid (213.6 g) (97%, Fluka) at room temperature for 4 days. The product was purified via the sodium salt, extraction into an inert organic solvent, and acidification. Yield 18%.

This material had an acid value of 169.9 mg KOH per g from the first end-point as determined by auto-titration with M/10 tetraethylammonium hydroxide (TEAH) in propan-2-ol, in the presence of bromophenol blue indicator.

B) Preparation of Antiwear Agent 2

A mixture of 1.0 g of PMH and 10.15 g PED was heated at 100° C. for approximately fifteen minutes to ensure reaction. This gave a partly neutralised organophosphorus salt of PED.

EXAMPLE 5

Antiwear Agent 3

A mixture of 1.0 g of bis(2-ethylhexyl) phosphate from BDH (having an acid value of 169.9 mg KOH per g by auto-titration with M/10 tetraethylammonium hydroxide (TEAH)) and 10.43 g PED was heated at 100° C. for approximately fifteen minutes to ensure reaction.

This gave a partly neutralised organophosphorus salt of PED.

EXAMPLE 6

Antiwear Agent 4

A mixture of 1.05 g O,O-bis(2-ethylhexyl) phosphoromonothioate (Hoechst) (having an acid value of 138.0 mg KOH per g by auto-titration with M/10 tetraethylammonium hydroxide (TEAH)) and 10.15 g PED was heated at 100° C. for approximately fifteen minutes to ensure reaction. This gave a fully neutralised organophosphorus salt of PED.

EXAMPLE 7

Antiwear Agent 5

A mixture of 1.0 g of O,O-diethyl phosphorodithioate (Aldrich) (having an acid value of 279.0 mg KOH per g by auto-titration with M/10 tetraethylammonium hydroxide (TEAH)) and 17.3 g PED was heated at 100° C. for approximately fifteen minutes to ensure reaction. This gave a fully neutralised organophosphorus salt of PED.

EXAMPLE 8

Antiwear Agent 6

A mixture of 0.5 g of n-octylphosphonic acid (Johnson Matthey) (having an acid value of 320.7 mg KOH per g by auto-titration with M/10 tetraethylammonium hydroxide (TEAH)) and 5.89 g PED was heated at 100° C. for approximately fifteen minutes to ensure reaction. This gave a 1:1 organophosphorus salt of PED.

EXAMPLE 9

Antiwear Agent 7

A mixture of 1.0 g of 2-ethylhexyl 2-ethylhexylphosphonate from BDH (having an acid value of 180.8 mg KOH per g by auto-titration with M/10 alcoholic potassium hydroxide solution using 1-naphthophthalein as indicator) and 11.24 g PED was heated at 100° C. for approximately fifteen minutes to ensure reaction.

This gave a fully neutralised organophosphorus salt of PED.

EXAMPLE 10

Antiwear Agent 8

A) Preparation of Dihexyl Pyrophosphate (DHP)

This phosphate was prepared as a mixture of symmetrical and non-symmetrical esters by reacting two mole of n-hexanol with one mole of phosphorous pentoxide in the method of J. H. Cronje, J. S. African Chem. Inst., 1949, 2, 15–27.

This material when titrated with M/10 alcoholic potassium hydroxide solution using 1-naphthophthalein as indicator had an acid value of 359 mg KOH per gram.

B) Preparation of Antiwear Agent 8

A mixture of 1.06 g of DHP and 23.5 g PED was heated at 100° C. for approximately fifteen minutes to ensure reaction. This gave a fully neutralised organophosphorus salt of PED.

EXAMPLE 11

Antiwear Agent 9

A) Preparation of Polyesteramine (PCD)

The Polyesteramine was obtained by the reaction of 55 g 6-caprolactone with 10 ml of 1-amino-3-N,N-dimethylaminopropane in the presence of 0.1 ml tetrabutyl titanate with stirring for 1.5 hr. at 160° to 165° C.

This amine when titrated with 0.1M hydrochloric acid, had an 'base' value of 15.69 mg KOH per gram.

B) Preparation of Mono Iso-octadecyl Phosphate (IOP)

A mixture of mono and di-iso-octadecyl phosphate was prepared by reacting three mole of iso-octadecanol with one mole of phosphorous pentoxide.

This material had an acid value of 169.9 mg KOH per g from the first end-point as determined by auto-titration with M/10 tetraethylammonium hydroxide (TEAH).

C) Preparation of Antiwear Agent 9

A mixture of 7.81 g of IOP and 12.96 g CPD was heated at 50° C. for about 20 minutes to ensure reaction. This gave a salt of PCD.

EXAMPLE 12

Antiwear Agent 10

A) Preparation of Polyesteramine (PEP)

The Polyesteramine was obtained by the reaction of one mole of poly(12-hydroxyoctadecanoic acid) of molecular weight about 1600 (as determined by titration) with two mole of piperazine dihydrate by heating, initially to 110° C. and after removing solvent to 170° C., to remove water and excess piperazine.

This amine when titrated with 0.1M perchloric acid in glacial acetic acid, had an 'base' value of 33.2 mg KOH per gram.

B) Preparation of Antiwear Agent 10

A mixture of 7.81 g of HP and 12.96 g PEP was heated at 50° C. for about 20 minutes to ensure reaction. This gave a fully neutralised salt of PEP.

EXAMPLE 13

Lubricants 2 to 10

Lubricant compositions 2 to 10 were prepared from each of the Antiwear Agents 2 to 10 respectively as described in Example 2.

EXAMPLE 14

A sample of each of Lubricants 2 to 8 and 10 was tested as described in Example 3 to determine its WSD, and these are recorded in Table 2.

TABLE 2

| Additive | WSD (mm) |
| --- | --- |
| Antiwear Agent 2 | 0.37 |
| Antiwear Agent 3 | 0.41 |
| Antiwear Agent 4 | 0.39 |
| Antiwear Agent 5 | 0.37 |
| Antiwear Agent 6 | 0.44 |
| Antiwear Agent 7 | 0.57 |
| Antiwear Agent 8 | 0.46 |
| Antiwear Agent 10 | 0.32 |

EXAMPLE 15

Lubricant 11

A lubricant composition 11 was prepared by adding 1 part of Antiwear Agent 9 to 99 parts of the synthetic ester di-iso-tridecyl phthalate (ICI C&P).

EXAMPLE 16

A sample of Lubricant 11 was tested as described in Example 3 to determine its WSD, and this is recorded in Table 3.

TABLE 3

| Additive | WSD (mm) |
| --- | --- |
| Antiwear Agent 9 | 0.52 |
| Nil | 0.92 |

EXAMPLE 18

Lubricant 12

A lubricant composition 12 was prepared by adding 1 part of Antiwear Agent 5 to 99 parts of a lithium hydroxystearate base grease with a total soap content of 9.4%.

EXAMPLE 16

A sample of Lubricant 12 was tested as described in Example 3 to determine its WSD, and this is recorded in Table 4.

TABLE 4

| Additive | WSD (mm) |
| --- | --- |
| Antiwear Agent 5 | 0.36 |
| Nil | 0.75 |

I claim:

1. An ammonium salt of an organo-oxyphosphorus acid, an organo-thiophosphorus acid or esters thereof with a polyesteramine of formula $$Y-CO-[O-A-CO]_n-Z-R$$

wherein

A is a divalent hydrocarbon radical;

Y is a hydrogen atom or an optionally substituted hydrocarbon group;

n is an integer from 1 to 100;

Z is a divalent bridging group; and

R is an amino group.

2. A salt as claimed in claim 1 wherein Y—CO— is 12-hydroxystearyl or 12-hydroxyoleyl.

3. A salt as claimed in claim 1 wherein n is from 1 to 10, and the group —O—A—CO— is 12-oxystearyl, 12-oxyoleyl or 6-oxycaproyl.

4. A salt as claimed in claim 1 wherein Z is of the formula $$-NQ-L- \text{ or } -O-L-$$

wherein

Q is hydrogen or alkyl;

L is alkylene or hydroxyalkylene; or

N, Q and L, together with the nitrogen atom in the group R to which they are attached form a cycloaliphatic bridging group.

5. A salt as claimed in claim 1 wherein R has the formula $$-N\begin{matrix}T^1\\ \diagdown\\ T^2\end{matrix}$$

wherein $T^1$ and $T^2$ are independently hydrogen, $C_{1-22}$ alkyl, substituted $C_{1-22}$ alkyl, alkaryl or cycloalkyl; or $T^1$ and $T^2$ together with the nitrogen atom to which they are attached form a 5- or 6-membered ring.

6. A salt as claimed in claim 1 wherein the organo-oxyphosphorus acid, organo-thiophosphorus acid or ester thereof has the formula $$\begin{matrix}X\\ \|\\ R^1-P-XH\\ |\\ X-(A-O-)_mR^2\end{matrix}$$

wherein $R^1$ is linear or branched alkyl, aralkyl, alkaryl, aryl, cycloalkyl, alkenyl or alkynyl, or a group [X]—X—(A—O—)$_m$R$^2$ or a group —X—P(X)—(XR$^2$)$_2$;

$R^2$ is hydrogen or optionally substituted $C_{1-30}$ hydrocarbyl;

A—O— is $C_{2-6}$ alkyleneoxy;

m is 0 to 50, and

X is oxygen or sulphur, provided that when m is zero, $R^1$ and $R^2$ are not both hydrogen.

7. A salt as claimed in claim 6 wherein the acid or ester thereof has the formula $$\begin{matrix}O\\ \|\\ R^5-P-OH\\ |\\ R^5\end{matrix}$$

wherein $R^5$ is independently a group —O—(A—O—)$_m$R$^2$; and $R^2$, A—O— and m are as defined;

provided that when m is zero, both $R^2$ are not hydrogen, or the formula $$\begin{matrix}S\\ \|\\ R^5-P-SH\\ |\\ R^5\end{matrix}$$

wherein $R^5$ is independently the group $-O-(A-O-)_m R^2$; and $R^2$, $A-O-$ and m are as defined;

provided that when m is zero, both $R^2$ are not hydrogen.

8. The ammonium salt formed from
   a) the reaction product of 2 mole poly(12-hydroxystearic acid) and 1 mole dimethylaminopropylamine; and
   b) di-n-hexylphosphate.

9. A lubricant composition comprising a lubricant and 0.01 to 10% by weight of an ammonium salt as claimed in claim 1.

10. A metal surface treated with an ammonium salt as claimed in any one of claims 1 to 8 or which is treated with a composition as claimed in claim 9.

* * * * *